United States Patent
Kim

[11] Patent Number: 6,141,092
[45] Date of Patent: Oct. 31, 2000

[54] METHOD AND APPARATUS FOR MEASURING A FLICKER LEVEL

[75] Inventor: Kyu-Seok Kim, Kyungki-do, Rep. of Korea

[73] Assignee: Samsung Electronics Co., Ltd., Rep. of Korea

[21] Appl. No.: 09/187,019

[22] Filed: Nov. 6, 1998

[30] Foreign Application Priority Data

Nov. 6, 1997 [KR] Rep. of Korea .................. 97-58439

[51] Int. Cl.[7] ................... G01J 1/60; A61B 3/10
[52] U.S. Cl. .................... 356/214; 351/211; 351/221
[58] Field of Search .................... 356/214, 213; 351/211, 204, 206, 210, 221; 324/770; 349/14

[56] References Cited

U.S. PATENT DOCUMENTS 5,276,539 1/1994 Humphrey .................... 349/14

Primary Examiner—Frank G. Font
Assistant Examiner—Roy M. Punnoose
Attorney, Agent, or Firm—Howrey Simon Arnold & White, LLP

[57] ABSTRACT

Disclosed is a method for measuring a flicker level. The method includes the steps of applying a first voltage to a liquid crystal display panel, the LCD panel including liquid crystal material and varying in transmissivity of light according to voltage applied to the liquid crystal material, such that light passing through the liquid crystal material is emitted from the LCD panel; detecting brightness of the light emitted from the LCD panel; determining a maximum brightness value and a minimum brightness value; and introducing the maximum brightness values and the minimum brightness value into a retina responsiveness function according to the brightness to attain flicker level values. The retina responsiveness function is a function of a strength of light passing through the pupil of the human eye. An inventive apparatus for measuring a flicker level includes a brightness detector for detecting brightness of light emitted from a liquid crystal display panel; a max/min brightness measuring portion for receiving input of brightness values from the brightness detector and determining a maximum brightness value and a minimum brightness value; and a flicker level measuring portion for attaining flicker level values by introducing the maximum and minimum brightness values input from the max/min brightness measuring portion into a retina responsiveness function according to brightness.

13 Claims, 4 Drawing Sheets

METHOD AND APPARATUS FOR MEASURING A FLICKER LEVEL

BACKGROUND OF THE INVENTION

1. Field of the Invention

The present invention relates to a method and apparatus for measuring a flicker level, and more particularly, to a method and apparatus for measuring a level of screen flicker visible to the human eye.

2. Description of the Prior Art

Liquid crystal displays (LCSs) are increasingly being used for the display device in televisions, personal computers, etc., and in many state-of-the-art equipment such as automotive navigation systems and simulation devices. LCDs are significantly lighter in weight and slimmer, consume far less energy and can reproduce a wider range of colors than any competing technologies.

LCDs apply an electric field to liquid crystal material having an anisotropic dielectricity and injected between two substrates, an array substrate and a counter substrate, arranged substantially parallel to one another with a predetermined gap therebetween, and control the amount of light permeating the substrates by controlling an intensity of the electric field to obtain a desired image signal.

Formed on the array substrate are a plurality of gate lines disposed parallel to one another, and a plurality of data lines insulated from and crossing the gate lines. A plurality of pixel electrodes are formed corresponding to respective regions defined by the intersecting data lines and gate lines. Further, a thin film transistor (TFT) is provided near each of the intersections of the gate lines and the data lines. Each pixel electrode is connected to a data line via a corresponding TFT, the TFT serving as a switching device therebetween.

Each TFT has a gate electrode, a drain electrode, and a source electrode, and the pixel electrodes are connected to the drain electrodes. Here, common electrodes are disposed on either the array substrate or the counter substrate.

The electric field applied to the liquid crystal material is generated by a difference in levels of common voltage and data voltage applied respectively to the common electrodes and the pixel electrodes provided in the LCD. An intensity of the electric field is controlled by changing data voltage or common voltage levels.

As the liquid crystal material degrades if the electric field is applied to the liquid crystal material continuously in the same direction, the direction in which the electric field is applied must be constantly changed. Namely, a value of the data voltage minus the common voltage must be repeatedly alternated from a positive value (hereinafter referred to as positive voltage) to a negative value (hereinafter referred to as negative voltage).

Such a switching of electrode voltage values between positive and negative values is referred to as inversion drive. Among the different types of inversion drive methods are frame inversion, line inversion, dot inversion, and column inversion methods.

In frame inversion, in which the polarity of data voltage is inverted to frame cycles (typically 60 Hz), positive voltage is applied in odd frames, while negative voltage is applied in even frames. Here, it is established such that a root mean square (RMS) of the positive voltage is the same as a RMS of the negative voltage.

However, in the actual performing of inversion drive in the LCD, kickback voltage is generated by parasitic capacitance in the pixels such that the RMS of the positive voltage comes to differ from the RMS of the negative voltage. Accordingly, a brightness of light permeating the liquid crystal material in the odd frames and that of light permeating the liquid crystal material in the even frames become dissimilar. This results in screen flickers generating in units of one-half of frame frequency of 60 Hz, or 30 Hz.

Such a screen flicker is measured using Formula 1 below introduced by the Apple Corporation $$F = 10 \log \frac{Pf}{Po} \qquad \text{[Formula 1]}$$

In the above Formula 1, F is the flicker level, and Po and Pf are amplitudes respectively of DC elements and AC elements (flicker elements) of light emitted from the LCD panel. Namely, according to the prior art flicker level measuring method, the level of screen flicker is the ratio of an amplitude of flicker elements to DC elements of light.

Referring to FIG. 1, shown is a graph illustrating Po and Pf of light emitted from an LCD panel. In the drawing, a brightness of light is realized by a sine function related to time, an average value (DC elements) of the sine function being Po, and an amplitude of the sine function being Pf. In FIG. 1, as Po is always larger than Pf, the flicker level attained using Formula 1 is always a negative value.

According to Formula 1, the flicker level is determined with considerations of merely the brightness of the light (DC elements and AC elements) emitted from the LCD panel, but other factors besides the brightness of the light such as screen size, distance between the screen and user, involuntary adjustment of the size of the pupil, etc. also determine the amount of screen flicker visible to the human eye. Accordingly, the flicker level attained using Formula 1 does not take into account these other factors.

Reasons why the flicker level attained using Formula 1 and the flicker level visible to the human eye are different will be explained hereinafter.

In Table 1 below, shown are DC elements Po and flicker elements Pf, and various flicker levels attained using Formula 1 when the difference in common voltage and data voltage is applied to 64 gray levels. A graph of the flicker levels according to gray levels of Table 1 is shown in FIG. 2.

TABLE 1

| Gray level | DC elements (Po) | Flicker elements (Pf) | Flicker level (F) |
|---|---|---|---|
| 1 | 0.83 | 0.01 | −23.86 |
| 5 | 0.88 | 0.01 | −22.03 |
| 9 | 1.01 | 0.02 | −17.63 |
| 13 | 1.24 | 0.04 | −14.87 |
| 17 | 1.83 | 0.05 | −15.32 |

TABLE 1-continued

| Gray level | DC elements (Po) | Flicker elements (Pf) | Flicker level (F) |
|---|---|---|---|
| 21 | 2.60 | 0.08 | −15.35 |
| 25 | 3.88 | 0.11 | −15.58 |
| 29 | 5.40 | 0.14 | −15.85 |
| 33 | 7.52 | 0.19 | −16.06 |
| 37 | 9.77 | 0.19 | −17.02 |
| 41 | 12.55 | 0.17 | −18.60 |
| 45 | 15.74 | 0.19 | −19.18 |
| 49 | 19.35 | 0.16 | −20.70 |
| 53 | 24.12 | 0.16 | −21.85 |
| 57 | 28.80 | 0.06 | −26.63 |
| 61 | 33.91 | 0.01 | −38.02 |
| 64 | 34.84 | 0.01 | −34.73 |

According to Table 1 and FIG. 2, a flicker level value attained using Formula 1 at a gray level of 13 is largest. However, in actuality, a flicker level visible to the human eye is largest at a more medium gray level of 32. Reasons for this will be explained hereinafter with reference to FIG. 3.

FIG. 3 is a graph illustrating transmissivity of light with regard to voltage Va applied to liquid crystal material of the LCD. In the drawing, light begins to transmit through liquid crystal material when the voltage Va applied to the same is above a threshold voltage Vth, with the transmissivity of light increasing as the voltage Va is increased. However, when the voltage Va exceeds a saturation voltage Vsat, the transmissivity of light no longer increases.

When the voltage Va applied to the liquid crystal material is at a point roughly in the middle level between the threshold voltage Vth and the saturation voltage Vsat, the transmissivity of light is greatly affected by even slight fluctuations in the voltage Va. Namely, small changes in the voltage Va in the middle level between the threshold voltage Vth and the saturation voltage Vsat produce large differences in light transmissivity. Accordingly, flickering is most visible to the human eye in this central gray voltage level.

Therefore, the prior method of calculating flicker levels is not accurate.

SUMMARY OF THE INVENTION

The present invention has been made in an effort to solve the above problem.

It is an object of the present invention to provide a method and apparatus for accurately measuring a level of screen flicker visible to the human eye.

To achieve the above object, the present invention provides a method for measuring a flicker level. The method includes the steps of applying a first voltage to a liquid crystal display panel, the LCD panel including liquid crystal material and varying in transmissivity of light according to the voltage applied to the liquid crystal material, such that light passing through the liquid crystal material is emitted from the LCD panel; detecting brightness of the light emitted from the LCD panel; determining a maximum brightness value and a minimum brightness value; and introducing the maximum brightness values and the minimum brightness value into a retina responsiveness function according to the brightness to attain flicker level values. The retina responsiveness function is a function of a strength of light passing through the pupil of the human eye.

An inventive apparatus for measuring a flicker level includes a brightness detector for detecting brightness of light emitted from a liquid crystal display panel; a max/min brightness measuring portion for receiving input of brightness values from the brightness detector and determining a maximum brightness value and a minimum brightness value; and a flicker level measuring portion for attaining flicker level values by introducing the maximum and minimum brightness values input from the max/min brightness measuring portion into a retina responsiveness function according to brightness.

BRIEF DESCRIPTION OF THE DRAWINGS

Further objects and other advantages of the present invention will become apparent from the following description in conjunction with the attached drawings, in which.

DESCRIPTION OF THE PREFERRED EMBODIMENT

A preferred embodiment of the present invention will now be described in detail with reference to the accompanying drawings.

Reaction to all external light is not direct with the human eye. That is, light must first pass through the pupil before it is reacted to by the retina. Further, as the size of the pupil varies according to different strengths of light, there is a difference in the strength of light reaching the retina of the eye and the actual strength of the external light.

The present invention takes into account this difference in the actual strength of external light and the strength of light reaching the retina.

The size, or diameter, of the pupil with regard to brightness is determined using Formula 2. The formula was developed by Degroot and Gebhard.

$$D(L) = 10^{0.8558 - 0.000401(\log L + 8.5)^{-3}}$$ Formula 2

In Formula 2, L is brightness, which is in a unit of cd/m2, and D(L) is a diameter of the pupil. As is obvious from Formula 2, the size of the pupil decreases as brightness increases.

As mentioned above, only the light passing through the pupil reaches the retina. The strength of the light (referred to as "trolands") reaching the retina can be calculated using Formula 3 below.

$$D(L) = \pi \times L \times \left(\frac{D(L)}{2}\right)^2 \qquad \text{[Formula 3]}$$

If D(L) of Formula 2 is introduced into Formula 3, the following Formula 4 results.

$$D(L) = \pi \times L \times \left(\frac{10^{0.8558-0.000401(\log L+8.6)^3}}{2}\right)^2 \qquad \text{[Formula 4]}$$

In Formula 4, TD(L) is the strength of light reaching the retina and is a function of brightness (L).

Figure 1:
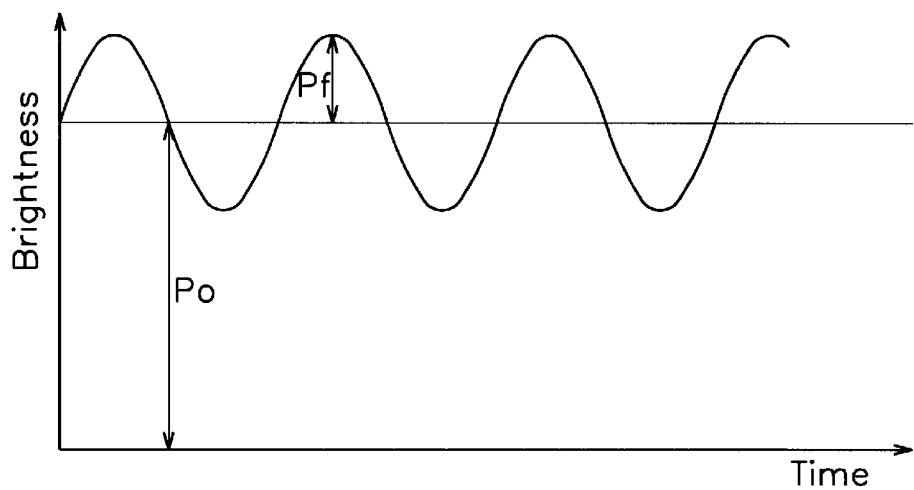
FIG. 1 is a graph illustrating DC elements and flicker elements of light emitted from an LCD panel.
Figure 2:
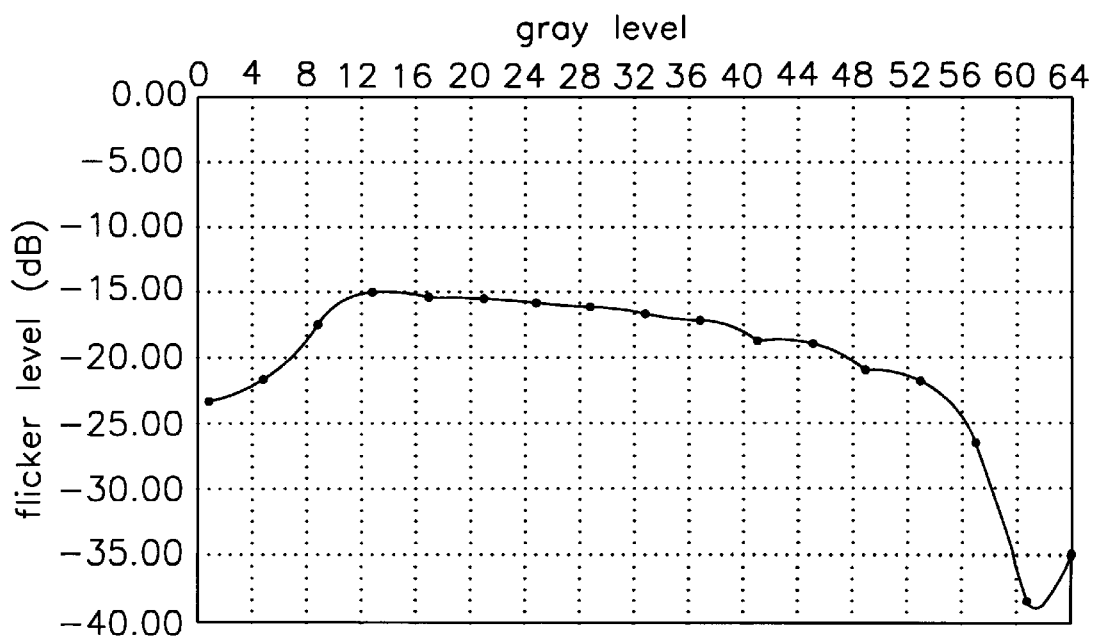
FIG. 2 is a graph of flicker levels according to gray levels of Table 1 in the specification, the flicker levels being measured using a prior art method.
Figure 3:
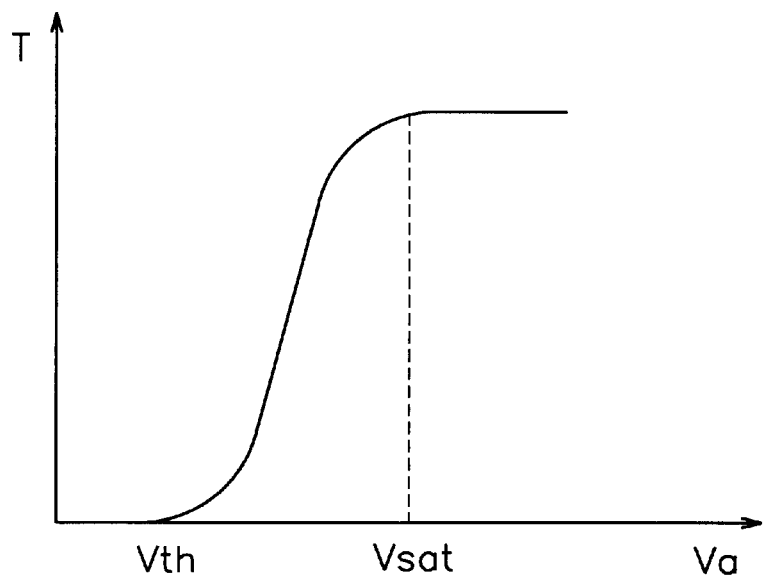
FIG. 3 is a graph illustrating transmissivity of light with regard to voltage applied to liquid crystal material of the LCD.
Figure 4:
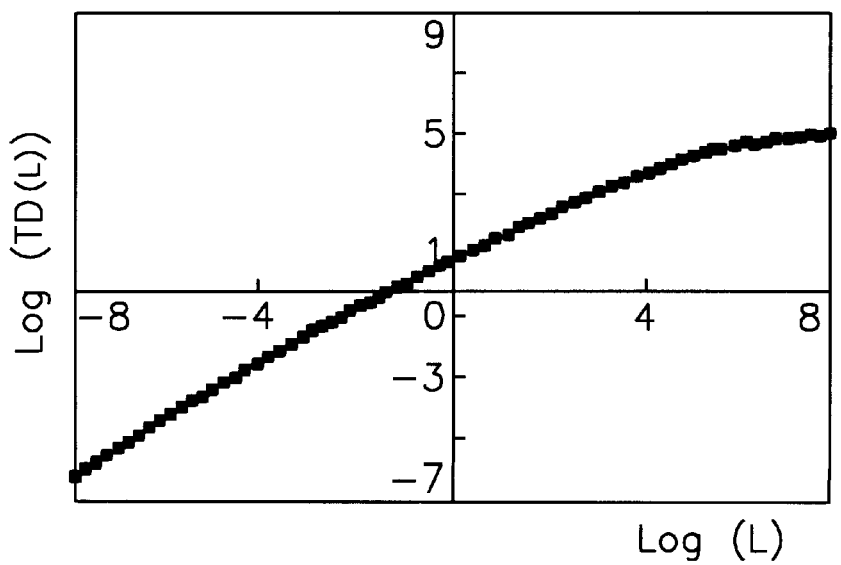
FIG. 4 is a graph illustrating an interrelation between brightness and a strength of light reaching a retina.

Referring to FIG. 4, shown is a graph illustrating an interrelation between brightness and the strength of light reaching the retina. A horizontal axis of the graph is a log value of brightness (L), while a vertical axis is a log value of the strength of light reaching the retina TD(L). As shown in the graph, the strength of light reaching the retina increases in a linear relation to an increase in brightness but only to a point, after which the increase in the amount of light reaching the retina tapers off, then eventually flattens such that there is no further increase in the amount of light reaching the retina with increases in brightness.

The light reaching the retina is converted into an electric signal through the retina membrane, and the electric signal is transmitted to the brain through optical nerves. The electric signal with respect to the strength of light passing through the pupil (i.e. eye responsiveness) is modeled using Formula 5 below.

$$R(L) = A \frac{TD(L)^{0.74}}{TD(L)^{0.74} + 1584.9^{0.74}} \qquad \text{[Formula 5]}$$

In Formula 5, also known as the Michaelis-Menten Equation, R(L) represents retina responsiveness. TD(L) is the strength of light reaching the retina, calculated using Formulas 3 and 4, and A is a constant. A is assumed to be 1000 in the preferred embodiment.

If TD(L) of Formula 4 is introduced into Formula 5, the following Formula 6 results.

$$R(L) = 1000 \frac{\pi \times L \times \left(\frac{10^{0.8558-0.000401(\log L+8.6)^3}}{2}\right)^{2 \times 0.74}}{\pi \times L \times \left(\frac{10^{0.8558-0.000401(\log L+8.6)^3}}{2}\right)^{2 \times 0.74} + 1584.9^{0.74}} \qquad \text{[Formula 6]}$$

Figure 5:
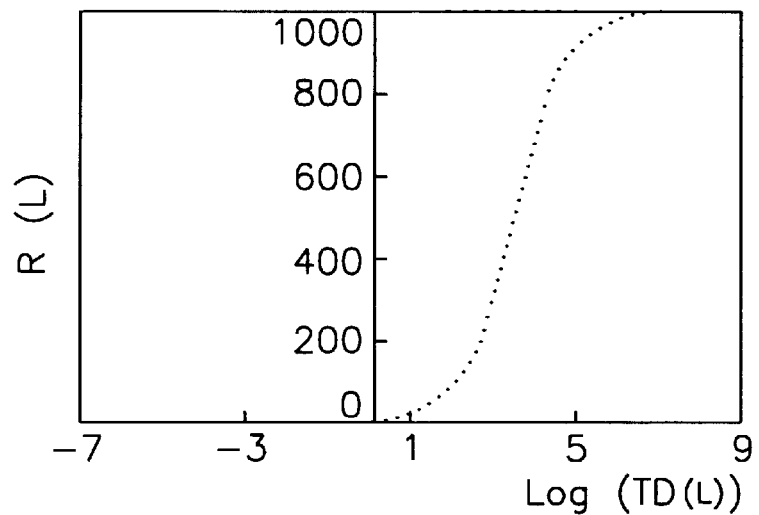
FIG. 5 is a graph illustrating a responsiveness of a retina to a strength of light reaching a retina.
Figure 6:
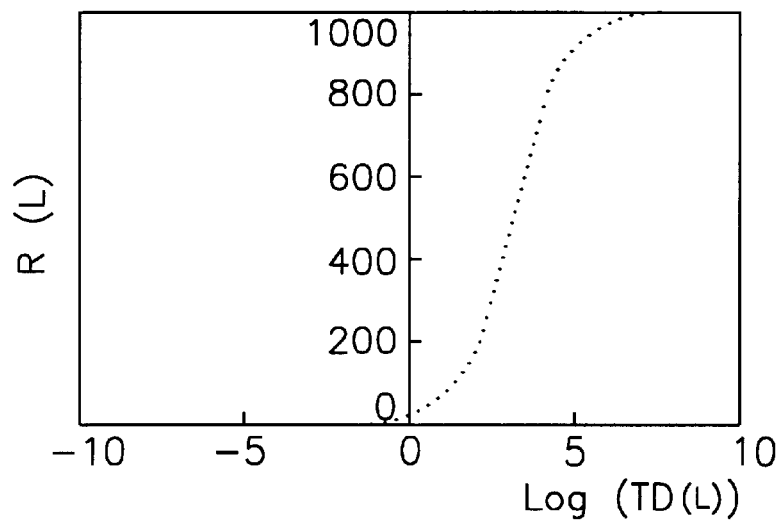
FIG. 6 is a graph illustrating a relation between brightness and retina responsiveness.

The strength of light reaching the retina TD(L), and responsiveness of the retina with respect to brightness (L) attained using Formula 6 are illustrated in FIGS. 5 and 6, respectively.

In FIG. 5, a horizontal axis of the graph is a log value log[TD(L)] of the strength of light reaching the retina TD(L), and a vertical axis is the responsiveness of the retina R(L). As shown in this graph, when the log value log[TD(L)] of the strength of light reaching the retina TD(L) is roughly 1 and under, the responsiveness of the retina R(L) is at or slightly above 0, and when the log value log[TD(L)] of the strength of light reaching the retina TD(L) is slightly above 5, the responsiveness of the retina R(L) is at 1000.

In FIG. 6, a horizontal axis is a log value Log(L) of brightness L, and a vertical axis is the responsiveness of the retina R(L). Here also, as in FIG. 5, the responsiveness of the retina R(L) is at zero at a predetermined log value Log(L) of brightness L, and at 1000 at a larger, predetermined log value Log(L) of brightness L.

In Formula 6 and FIG. 6, retina responsiveness R(L) varies when brightness L is at a maximum value and minimum value. In the present invention, these values are determined as flicker levels. Formula 7 below is used in the present invention to calculate flicker levels.

$$F = R(Lmax) - R(Lmin) = R(Po+Pf) - R(Po-Pf) \qquad \text{Formula 7}$$

In the above Formula 7, Lmax indicates a maximum value of brightness, and Lmin indicates a minimum value of brightness. The maximum value of brightness Lmax is attained by adding a brightness DC element value Po to a flicker element amplitude Pf, while the minimum value of brightness Lmin in attained by subtracting the flicker element amplitude Pf from the brightness DC element value Po. The following Formula 8 results by introducing Formula 6 into Formula 7.

$$F = 1000\frac{\pi \times Lmax \times \left(\frac{10^{0.8558-0.000401\,(\log Lmax+8.6)^3}}{2}\right)^{2\times 0.74}}{\pi \times Lmax \times \left(\frac{10^{0.8558-0.000401\,(\log Lmax+8.6)^3}}{2}\right)^{2\times 0.74} + 1584.9^{0.74}} -$$

$$1000\frac{\pi \times Lmin \times \left(\frac{10^{0.8558-0.000401\,(\log Lmin+8.6)^3}}{2}\right)^{2\times 0.74}}{\pi \times Lmin \times \left(\frac{10^{0.8558-0.000401\,(\log Lmin+8.6)^3}}{2}\right)^{2\times 0.74} + 1584.9^{0.74}}$$

[Formula 8]

Results of flicker levels calculated using Formula 8 appear in Table 2 below. In Table 2, as in Table 1 appearing in the Background of the Invention section of this specification, shown are DC elements Po and flicker elements Pf, and various flicker levels attained using Formula 1 when the difference in common voltage and data voltage is applied to 64 gray levels, in addition to maximum and minimum values of brightness Lmax and Lmin.

TABLE 2

| Gray level | DC elements (Po) | Flicker elements (Pf) | Lmax | Lmin | Flicker level (F) |
|---|---|---|---|---|---|
| 1 | 0.83 | 0.01 | 0.84 | 0.82 | 0.12 |
| 5 | 0.88 | 0.01 | 0.89 | 0.87 | 0.19 |
| 9 | 1.01 | 0.02 | 1.03 | 0.99 | 0.55 |
| 13 | 1.24 | 0.04 | 1.28 | 1.20 | 1.18 |
| 17 | 1.83 | 0.05 | 1.68 | 1.78 | 1.30 |
| 21 | 2.60 | 0.08 | 2.68 | 2.52 | 1.56 |
| 25 | 3.88 | 0.11 | 3.99 | 3.77 | 1.81 |
| 29 | 5.40 | 0.14 | 5.54 | 5.26 | 1.99 |
| 33 | 7.52 | 0.19 | 7.71 | 7.33 | 2.22 |
| 37 | 9.77 | 0.19 | 9.96 | 9.58 | 2.00 |
| 41 | 12.55 | 0.17 | 12.72 | 12.38 | 1.55 |
| 45 | 15.74 | 0.19 | 15.93 | 12.55 | 1.49 |
| 49 | 19.35 | 0.16 | 19.51 | 19.19 | 1.14 |
| 53 | 24.12 | 0.16 | 24.28 | 23.96 | 0.95 |
| 57 | 28.80 | 0.06 | 28.86 | 28.74 | 0.34 |
| 61 | 33.91 | 0.01 | 33.92 | 33.90 | 0.03 |
| 64 | 34.84 | 0.01 | 34.85 | 34.83 | 0.06 |

Figure 7:
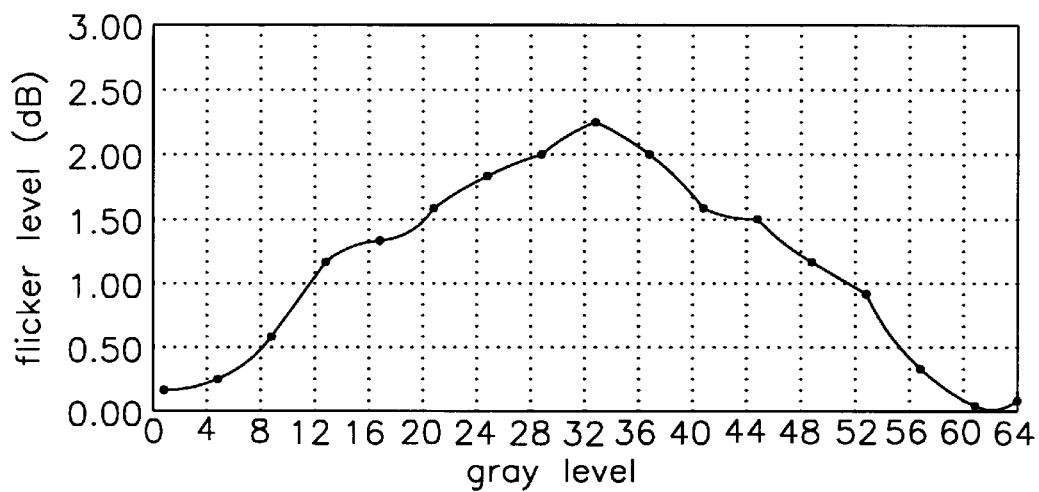
FIG. 7 is a graph of flicker levels according to gray levels of Table 2 in the specification, the flicker levels being measured using an inventive method.

As shown in FIG. 7, illustrating a graph of flicker levels according to the gray levels of Table 2, the flicker level values are the highest at a gray level of roughly 32. That is, flicker levels visible to the human eye are the largest at such medium gray levels.

In the above, the size (diameter) of the pupil D(L) according to brightness L is determined using Formula 2. The same can also be calculated using Formula 9 below developed by Moon and Spenser.

$$D(L) = 4.9 - 3\tanh[0.4(\log L + 1.0)] \quad \text{Formula 9}$$

The strength of light reaching the retina TD(L) and the responsiveness of the retina R(L) are able to be attained by introducing Formula 9 into Formulas 3 and 5, respectively, and flicker levels can be determined using these formulas. Flicker levels calculated in this manner come very to close to those actually recognized by the human eye.

Figure 8:
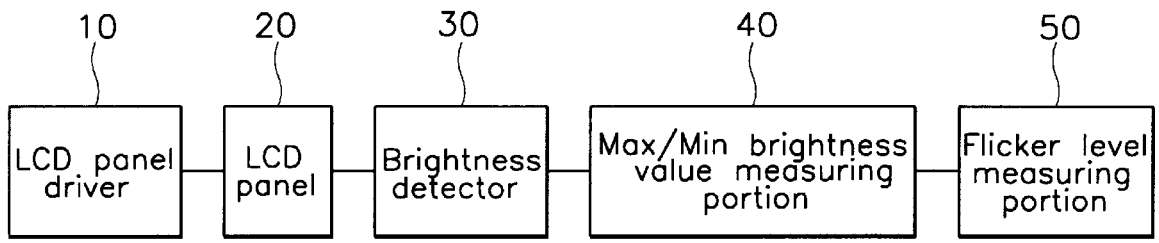
FIG. 8 is a block diagram of an apparatus for measuring flicker levels according to a preferred embodiment of the present invention.

Referring now to FIG. 8, shown is a block diagram of an apparatus for measuring flicker levels according to a preferred embodiment of the present invention, as shown in the drawing, the inventive apparatus for measuring flicker levels comprises an LCD panel driver 10, an LCD panel 20 driven by various drive voltages output by the LCD panel driver 10, a brightness detector 30 for detecting brightness of the LCD panel 20, a max/min brightness measuring portion 40 for receiving input of brightness values from the brightness detector 30 and determining a maximum brightness value Lmax and a minimum brightness value Lmin, and a flicker level measuring portion 50 for determining flicker levels using Formula 8 and the maximum and minimum brightness values Lmax and Lmin input from the max/min brightness measuring portion 40.

The brightness detector 30 is vertically disposed to the LCD panel 20, and it is preferable to provide at least one brightness detector 30 on the LCD panel 20. In the preferred embodiment of the present invention, brightness detectors 30 are provided at the center and at each corner of the LCD panel 20 for the better measurement of the brightness of the LCD panel 20.

In the inventive apparatus for measuring flicker levels as shown in FIG. 8, flicker levels are measured by changing gray levels of gray voltage, the gray voltage being applied to the LCD panel 20 from the LCD panel driver 10. A maximum value of measured flicker level values is attained, and this value is determined to be the flicker level of the LCD panel 10.

An example of an apparatus for measuring flicker levels will be described hereinafter.

The BM-7 measuring apparatus developed by TOCON of Japan is an example of a flicker measuring apparatus that is provided adjacent to the LCD panel to detect brightness. The BM-7 device receives input of brightness from the LCD panel and outputs the same as analog voltage Vout. The equation used for this process is listed below in Formula 10.

$$\text{Vout} = 0.0105 \times L \quad \text{Formula 10}$$

As described above, the maximum value of brightness Lmax and the minimum value of brightness Lmin must be defined to determine flicker levels, and the maximum and minimum values of brightness are attained using a DC element value of brightness Po and an amplitude value of AC elements (flicker elements) Pf. Here, brightness DC elements Po is a frequency of 0 Hz, and brightness AC elements Pf is a frequency of 30 Hz in the case of frame inversion.

However, because voltage output Vout from the BM-7 device is not output as voltage of each brightness (frequency) but as a sum of all ranges of frequencies, it is not possible to directly measure brightness values of the LCD panel from the voltage output from the BM-7 device.

Accordingly, Hewlett Packard's dynamic signal analyzer (model No. HP35665) is connected to the BM-7 device, and the output of voltage Vout from the same is used as input by the dynamic signal analyzer (DSA). Here, the DSA output voltage Vrms is converted into Formula 11 below.

$$Vrms = 20\log\left(\frac{Vout}{Vref}\right) \qquad \text{[Formula 11]}$$

In the above, Vref is a standard voltage, which is:

$$7.08\left(10^{\frac{17}{20}}\right)V.$$

As DSA output Vrms is output at each frequency, voltage Vout of each brightness can be attained. Provided that a DSA output of 0 Hz frequency is Vrms(0 Hz), and a DSA output of 30 Hz frequency is Vrms(30 Hz). Formula 11 is used to attain Vout(0 Hz) and Vout(30 Hz).

$$Vout(0\,Hz) = Vref \times 10^{\frac{Vrms(0Hz)}{20}},$$
$$Vout(30\,Hz) = Vref \times 10^{\frac{Vrms(30Hz)}{20}}$$

By introducing Vout(0 Hz) and Vout(30 Hz) above in Formula 10, L(0 Hz) and L(30 Hz) can be attained. Here, L(0 Hz) and L(30 Hz) are respectively the DC element value of brightness and the amplitude value of AC elements.

Accordingly, maximum and minimum values of brightness can be attained from L(0 Hz) and L(30 Hz), and by introducing the maximum and minimum values of brightness into Formula 8, flicker values can be measured.

In the above inventive method and apparatus, as flicker levels are measured taking into account pupil diameters and retina responsiveness, a more accurate measurement of flicker levels that is recognized by the human eye is realized.

While this invention has been described in connection with what is presently considered to be the most practical and preferred embodiment, it is to be understood that the invention is not limited to the disclosed embodiments, but, on the contrary, is intended to cover various modifications and equivalent arrangements included with the spirit and scope of the appended claims.

What is claimed is:

1. A method for measuring a flicker level, comprising the steps of:
    apply a voltage to a liquid crystal display (LCD) panel such that light passing through liquid crystal material provided in the LCD panel is emitted from the LCD panel, the LCD panel varying in transmissivity of light according to the voltage applied to the LCD panel;
    detecting a brightness L of the light emitted from the LCD panel;
    determining a maximum brightness value Lmax and a minimum brightness value Lmin; and
    introducing the maximum brightness value Lmax and the minimum brightness value Lmin into a retina responsiveness function according to the brightness L to attain a flicker level value of R(Lmax)−R(Lmin),
    wherein the retina responsiveness function is a function of a strength of light passing through a pupil of human eyes.

2. The method of claim 1, wherein the voltage is a gray voltage having a plurality of gray levels and a maximum value of flicker levels among all the flicker levels corresponding to the plurality of gray levels is determined as a flicker level of the LCD panel.

3. The method of claim 2, wherein the strength of light passing through the $$\text{pupil is } TD(L) = \pi \times L \times \left(\frac{D(L)}{2}\right)^2$$

where D(L) is a diameter of the pupil responding to brightness L.

4. The method of claim 3, wherein the diameter of the pupil is $$D(L)=10^{0.8558-0.000401(\log L+8.5)^3}.$$

5. The method of claim 3, wherein the diameter of the pupil is $$D(L)=4.9-3\tanh[0.4(\log L+1.0)]$$

6. The method of claim 4, wherein the retina responsiveness function is $$R(L) = A\frac{TD(L)^{0.74}}{TD(L)^{0.74} + 1584.9^{0.74}}$$

where A is a constant.

7. The method of claim 6, wherein A is 1000.

8. An apparatus for measuring a flicker level comprising:
    a brightness detector for detecting brightness of light emitted from a liquid crystal display panel;
    a max/min brightness measuring portion for receiving input of brightness values from the brightness detector and determining a maximum brightness value and a minimum brightness value; and
    a flicker level measuring portion for attaining flicker level values R(Lmax)−R(Lmin) by introducing the maximum and minimum brightness values Lmax and Lmin input from the max/min brightness measuring portion into a retina responsiveness function R(L) according to brightness L,
    wherein the retina responsiveness function is a function of a strength of light passing through the pupil of the human eye.

9. The apparatus of claim 8, wherein the strength of light passing through the $$\text{pupil is } TD(L) = \pi \times L \times \left(\frac{D(L)}{2}\right)^2$$

where D(L) is a diameter of the pupil responding to brightness L.

10. The apparatus of claim 9, wherein the diameter of the pupil is $$D(L)=10^{0.85-000401(\log L+8.6)^3}.$$

11. The apparatus of claim 9, wherein the diameter of the pupil is $$D(L) = 4.9 - 3\tanh[0.4(\log L + 1.0)]$$

12. The apparatus of claim 10, wherein the retina responsiveness function is $$R(L) = A \frac{TD(L)^{0.74}}{TD(L)^{0.74} + 1584.9^{0.74}}$$

where A is a constant.

13. The apparatus of claim 11, wherein the retina responsiveness function is $$R(L) = A \frac{TD(L)^{0.74}}{TD(L)^{0.74} + 1584.9^{0.74}}$$

where A is a constant.

* * * * *